(12) United States Patent
Fleming

(10) Patent No.: US 6,811,549 B2
(45) Date of Patent: Nov. 2, 2004

(54) ADMINISTRATION OF THERAPEUTIC OR DIAGNOSTIC AGENTS USING INTERLABIAL PAD

(76) Inventor: William H. Fleming, 18820 SW. Neugebauer Rd., Hillsboro, OR (US) 97123

( * ) Notice: Subject to any disclaimer, the term of this patent is extended or adjusted under 35 U.S.C. 154(b) by 241 days.

(21) Appl. No.: 09/788,264

(22) Filed: Feb. 16, 2001

(65) Prior Publication Data

US 2002/0115976 A1 Aug. 22, 2002

(51) Int. Cl.[7] .................................................. A61F 13/20
(52) U.S. Cl. ........................... 604/385.17; 604/385.18; 604/515; 604/904
(58) Field of Search ................... 604/904, 359, 604/360, 367, 363, 515, 385.19, 385.17; 424/76.1–76.5; 205/155

(56) References Cited

U.S. PATENT DOCUMENTS

| | | | |
|---|---|---|---|
| 3,983,873 A | | 10/1976 | Hirschman |
| 4,095,542 A | | 6/1978 | Hirschman |
| 4,142,476 A | | 3/1979 | Hirschman |
| 4,286,596 A | * | 9/1981 | Rubinstein ............... 604/244 |
| 4,340,055 A | | 7/1982 | Sneider |
| 4,920,045 A | | 4/1990 | Okuda et al. |
| 4,995,150 A | | 2/1991 | Gerstenberger et al. |
| 5,045,447 A | | 9/1991 | Minson |
| 5,074,855 A | * | 12/1991 | Rosenbluth et al. ... 604/385.17 |
| 5,094,956 A | | 3/1992 | Grow et al. |
| 5,124,252 A | | 6/1992 | Guerrant et al. |
| 5,190,881 A | | 3/1993 | McKibbin |
| 5,283,171 A | | 2/1994 | Manos et al. |
| 5,447,839 A | | 9/1995 | Manos et al. |
| 5,459,034 A | | 10/1995 | Tabaqchali et al. |
| 5,527,534 A | * | 6/1996 | Myhling ................... 424/430 |
| 5,538,851 A | | 7/1996 | Fach et al. |
| 5,563,071 A | | 10/1996 | Augurt |
| 5,575,047 A | | 11/1996 | Gerstenberger et al. |
| 5,580,907 A | | 12/1996 | Savin |
| 5,627,275 A | | 5/1997 | Roll |
| 5,661,010 A | | 8/1997 | De Lourdes Muñoz Moreno |
| 5,705,332 A | | 1/1998 | Roll |
| 5,783,412 A | | 7/1998 | Morris et al. |
| 5,855,906 A | | 1/1999 | McClay |
| 5,876,922 A | | 3/1999 | Orth et al. |
| 5,965,375 A | | 10/1999 | Valkirs |
| 5,968,026 A | | 10/1999 | Osborn, III et al. |
| 6,409,713 B1 | * | 6/2002 | Osborn et al. ......... 604/385.17 |

OTHER PUBLICATIONS

Saltzman et al., *Biotechnology and Bioengineering* 67(3):253–264 (2000).

* cited by examiner

*Primary Examiner*—John J. Calvert
*Assistant Examiner*—Jacqueline F. Stephens
(74) *Attorney, Agent, or Firm*—Klarquist Sparkman, LLP (57) ABSTRACT

A drug or diagnostic agent) is delivered intravaginally or to the interlabial space by positioning an interlabial device, such as an absorbent pad, between the labia. The pad is retained between the labia to deliver an active agent, or allow a reaction with a diagnostic agent. Alternatively, the pad is applied after medication is administered, to help reduce discomfort to the subject, or loss of medication. The active agent may be carried by the pad itself, or in an intravaginal extension of the pad, or separately in a suppository or other dosage form. In particular examples, the pad has a smaller minor portion superimposed on a larger major portion, and the smaller minor portion is inserted as a leading edge between the labia of the subject to facilitate interlabial insertion. In another example, the pad is placed interlabially after insertion of an agent into the vagina.

35 Claims, 7 Drawing Sheets

MRI of Pad and Tampon

ADMINISTRATION OF THERAPEUTIC OR DIAGNOSTIC AGENTS USING INTERLABIAL PAD

FIELD OF THE INVENTION

This invention relates to a drug delivery device, and more particularly to such a device that is capable of interlabial drug delivery, for example interlabial or peri-labial drug delivery, or can be used as an adjunct in the delivery of drugs.

BACKGROUND OF THE INVENTION

The female external genitalia includes the interlabial space, located between the inside surfaces of the labia majora and extending past the vestibule of the vagina. Located within this interlabial space are the labia minora, clitoris, urethral orifice, and vaginal orifice. The interlabial space is covered by a thin layer of keratinized epithelium.

A variety of diseases affect the interlabial space in human females. Infectious diseases include vaginitis, herpes simplex virus-2 (HSV-2), human papilloma virus (HPV), syphilis, and candidiasis. Dysplastic and hyperplastic conditions include postmenopausal atrophy, squamous cell hyperplasia, and lichen sclerosus. Precancerous and cancerous conditions include vulvar intraepithelial neoplasia and vulvar carcinoma. These diseases result in serious health problems, including pain, itching, disfigurement and possibly even death.

Currently, therapy for vulvar diseases is delivered either systemically or locally. Examples of systemic therapy include oral acyclovir for HSV-2 infection, and intramuscular penicillin-G for primary syphilis. Local therapy includes a variety of creams, ointments, and solutions containing corticosteroids, antifungal agents, hormones, and other medicinal agents.

Although both forms of therapy have shown favorable effects on many vulvar diseases, both have limitations. Systemic therapy carries the risk of systemic side effects, and the effectiveness of local therapy has been limited by the need for frequent applications, messiness, and poor patient compliance. There is a need, therefore, for a simple and effective approach to local therapy of vulvar diseases. At the same time, there is a need for more efficient, convenient and comfortable systemic administration of drugs, whether or not they are intended for the treatment of vulvar pathologies.

Feminine hygiene pads consisting of various layers of absorbent materials are used primarily to absorb uncontrolled discharges during menstruation. These pads have taken the form of thick elongated feminine napkins which are primarily used during the early stages of the menstrual cycle and narrow absorbent tubes, known as tampons, which are inserted into the vagina and which are used primarily during the latter stages of the menstrual cycle.

SUMMARY OF THE DISCLOSURE

The methods and devices of the present invention take advantage of a completely new use of absorbent interlabial pads, namely the administration of therapeutic and diagnostic agents, such as pharmaceutically active agents or diagnostic reagents. It has been found that local and transdermal administration of many different agents can be facilitated by application of the drug to the labia. However, because of the complex and sensitive anatomy of the perineum and associated labial tissue, it has been difficult to administer agents in this fashion. Moreover, the labial and peri-labial area is frequently the site of infection and inflammation (such as that caused by fungal or bacterial infections, such as vaginitis, or exposure to feces or urine). Although topical ointments can be applied to the perineum and labia, such topical administration is often messy and stains undergarments. In addition, intravaginal suppositories leak from the vagina, resulting in loss of some therapeutic efficacy, and discomfort to the subject.

The present invention has solved many of these problem, by providing a system or device for administering agents (such as pharmaceutically active substances or diagnostic reagents), wherein the device is configured to be retained between the labia of a subject. The device either carries a therapeutically or diagnostically effective amount of an agent to be delivered, or is placed interlabially after an agent has been applied, for example to the external genitalia or intravaginally (as with a suppository). In one example, the device includes an interlabial pad, which is retained in the interlabial space for sustained contact with the labial skin and/or vaginal orifice. This sustained contact conforms to the complex external genital and perineal anatomy, without causing additional discomfort. Moreover, the system is able to function as a self-contained transdermal interlabial drug delivery system which targets the delivery of certain medications to the labia and/or vagina, substantially without staining undergarments or inadvertently delivering the drug to the surrounding perineum and thighs. The pad can be retained in the interlabial space, without the use of a supporting garment or adhesive. In particular embodiments, the pad is positioned external to the vaginal orifice, so that it is not retained by insertion into the vagina. However, in other embodiments, a portion of the pad can project at least partially into the vagina for targeted delivery of drug to the intravaginal space.

In another embodiment, the delivery device includes an intravaginal portion and an extravaginal protion. The extravaginal portion can include an interlabial pad that is retained between the labia, and the intravaginal portion (such as a medicated extension or suppository) delivers medication intravaginally.

Although targeted local delivery of active agents is possible, particularly for an agent having low lipid permeability and low transdermal flux, the delivery system can also be used for systemic delivery of pharmaceutical agents through the labial skin, or via vaginal absorption.

BRIEF DESCRIPTION OF THE DRAWINGS

FIG. 4 is a cross sectional fragmentary view of another embodiment of the interlabial drug delivery pad.

FIGS. 5–9 are views similar to FIG. 4, but showing different embodiments of the pad which have a substantially quadrilateral shape.

FIGS. 10 and 11 are cross sectional views of the major portion of the pad, showing the major portion to be either arcuate (FIG. 10) or tapered (FIG. 11).

FIG. 12 is a cross sectional view of an interlabial absorbent pad that does not have a major portion and a minor portion, but which has the side surfaces of the pad sloping toward a leading edge of the pad.

FIGS. 13–15 are cross-sectional fragmentary views showing pads which have major portions that are polygonal in shape.

FIG. 16 is a cross sectional view of an elongated interlabial pad with a major portion and a minor portion, both of which taper symmetrically in a longitudinal direction.

FIG. 17 is a view similar to FIG. 16, but showing the major and minor portions of the pad tapering longitudinally in different directions.

DESCRIPTION OF MULTIPLE SPECIFIC EXAMPLES

The interlabial pad is used in a method of delivery of a therapeutic or diagnostic agent (such as a drug or diagnostic reagent) by positioning the absorbent pad between the labia, external to the subject's vaginal orifice, such that the pad is retained between and by the labia. In particular embodiments of this method, the pad is devoid of corners and flat surfaces intermediate its ends, and the pad has a minor portion superimposed on a major portion. The minor portion of the pad has a cross-sectional area or width that is smaller than a cross-sectional area or width of the major portion, and both the minor and the major portions are curvilinear or partially cylindrical in cross-section. The reduced width minor portion facilitates insertion of the pad between the subject's labia, separation of the labia, and placement of the smaller portion adjacent the vaginal orifice. The larger major portion conforms to the interlabial space, and helps hold the pad frictionally engaged in the space.

An example of an interlabial pad useful with the present methods is the interlabial pad developed by A-Fem Medical Corporation. Various forms of interlabial pads, as well as methods of producing them, are described in U.S. Pat. Nos. 3,983,873, 4,095,542 and 4,142,476. These pads are designed to be placed longitudinally between the vaginal lips or labia, and are particularly useful to absorb light discharges of menstrual fluids, mid-cycle spotting or discharges, slight loss of urine caused by physical stress, or leakages following intercourse.

Methods and devices for manufacturing feminine hygiene interlabial pads are described in U.S. Pat. No. 4,995,150, which patent is hereby incorporated herein by reference. However, in the embodiment as set forth in U.S. Pat. No. 4,995,150, it is taught that the outer covering be made of a heat-sealable material such as polypropylene, which is not easily biodegradable. A biodegradable interlabial pad is disclosed in U.S. Pat. No. 5,575,047, which is also incorporated by reference. The biodegradable pad is capable of being decomposed by natural biological processes.

Another example of an interlabial pad suitable for use with the present method is the absorbent interlabial device disclosed in U.S. Pat. No. 5,968,026, which issued to the Procter & Gamble Company, and which is incorporated by reference herein. A commercially available example of this pad is the Envive Miniform.

However, the invention is not limited to these specific particularly disclosed embodiments, which are only given by way of illustration. Any configuration of the pad is possible, which allows it to be capable of being substantially retained in the interlabial space by engagement with the labial folds, but can be simply and easily removed by manually removing it. Alternatively, the pad can be displaced by the application of liquid pressure during urination.

The retention of the pad in the interlabial space permits sustained contact between the pad and the labial skin, for sustained delivery of an active agent to the labial skin. Either local delivery to the labia, intravaginal delivery, or transdermal systemic delivery of drugs can be achieved. In particular embodiments, a method is disclosed for treating labial and vaginal inflammations by inserting the pad between the labia, against the external vaginal orifice.

Figure 32A:
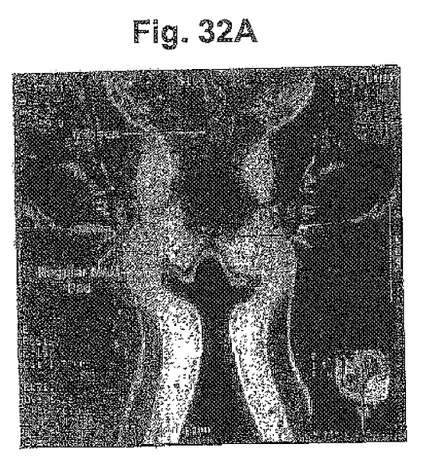
FIG. 32A is an MRI of an external feminine hygiene pad in place against the external female genitalia.
Figure 32B:
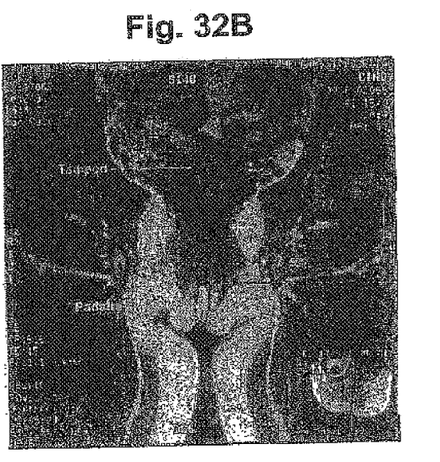
FIG. 32B is an MRI of an example of a pad in accordance with the present disclosure, in which the pad is retained between the labia, external to the hymenal ring

In some embodiments, the method delivers therapeutic substances (such as antibiotics, topical anesthetics or topical anti-fungal medication), for example in the treatment of vaginitis or dermatitis. The method includes positioning the interlabial pad such that the pad is retained between the labia external to the subject's vagina. The anterior portion of the pad is designed for insertion of the pad between the subject's labia in the anatomic interlabial space adjacent to the vaginal orifice, and the posterior portion is retained between the labia without the need for adhesive or other attachment devices, as in FIG. 32B. Alternatively, a portion of the pad can project into the vagina, for example to improve retention and enhance intravaginal delivery of an agent.

The pad can be any of a variety of shapes, and particularly shapes which taper toward an anterior or leading edge of the pad. The anterior edge is often sufficiently wide to be retained outside the vaginal orifice, but can be sufficiently narrow to extend at least partially within the vagina (for example no more than 1 inch into the vagina, and in some examples less than ½ inch). When the pad is substantially or completely retained external to the vagina, the posterior edge impinges against the surrounding labia to retain the pad in place. The pad can be symmetric or asymmetric, rounded or elongated, tapering or non-tapering, folded or not folded. However particular embodiments taper from a relatively larger posterior portion to a relatively smaller anterior portion. The enlarged posterior portion is often large enough to at least slightly deform the surrounding labia to improve frictional engagement between the labia and the pad. The relatively small anterior portion may in some examples be closer to the width of the vaginal orifice, and is more comfortably retained in the narrow interlabial space adjacent the vaginal orifice. The pads with a bipartite structure (with a major and minor portion) further enhance the comfort and retention of the pad.

The approach disclosed herein takes advantage of an interlabial route of administration, through an accessible, non-parenteral route, which is highly perfused with a well-developed blood supply that avoid first pass metabolism of the drug in the liver. It is a relatively non-invasive route (for example, avoiding the risks of IV non-parenteral administration), that takes advantage of high permeability for a penetrant having physiochemical characteristics that allow it to pass through the epithelial covering of the labia.

The permeability of vaginal epithelium has been found to be significantly greater than many other trans-mucosal routes, and the ILP can be used to deliver drugs intravaginally as well as to the vulvar or labial structures. The delivery device can therefore carry active agents for local or systemic effects. Examples of drugs suitable for delivery using the ILP are agents that are designed to exert a local effect, such as barrier contraception, treatment or prevention of infection, or estrogenization of vaginal epithelium. Examples of systemic pharmaceutical agents that can be delivered include steroid hormones for contraception or estrogen/hormone replacement therapy, or anti-infectives (such as antibiotics). The vaginal route is also believed to be an efficient route for the delivery of peptide and protein drugs, that are becoming increasingly important elements of the therapeutic armamentarium.

The interlabial delivery device can also be used in conjunction with other forms of drug delivery, such as topical ointments or creams, or intravaginal suppositories. For example, the ILP can be put in place after application of an external ointment or cream, or after insertion of the suppository, to increase comfort and decrease leakage or staining of garments. The ILP can be used, for example, with mucoadhesive drugs or solid hydrogels.

The following definitions and methods are provided to better define the present invention and to guide those of ordinary skill in the art in the practice of the invention. As used herein and in the appended claims, the singular forms "a", "an", and "the" include plural referents unless the context clearly dictates otherwise. Thus, for example, reference to "a material" includes a plurality of such materials, and reference to "the absorbent material" includes reference to one or more materials, and so forth.

Unless defined otherwise, all technical and scientific terms used herein have the same meaning as commonly understood by one of ordinary skill in the art to which this invention belongs.

Definitions

Absorbent: A material with sufficient absorbency to absorb and retain exudates discharged from a subject. Absorbency is dependent partially on the physical volume of the device. In a specific non-limiting example, a material is absorbent if it absorbs at least 3 ml of 0.9% saline, however an absorbent material may have a capacity of 20 grams or more.

Agent: A substance capable of producing a physical, chemical or biological effect. Examples of agents include drugs (therapeutic agents) and diagnostic reagents (diagnostic agents). Examples of drugs include antimicrobial agents (such as the anti-fungal agent miconozole, anti-viral acyclovir, or anti-biotic metronidazole). Examples of diagnostic agents include monoclonal antibodies (such as monoclonal antibodies that recognize human papillomavirus (HPV) or herpes simplex virus (HSV), or chemical reagents in which a reaction occurs in the presence of a pathogen of interest, such as a color change).

Biodegradable material: A material having greater than or equal to about 70% biodegradation (percentage of theoretical carbon dioxide evolution) after 28 days when measured by a suitable test such as the Sturm test (Method 301B, Organization of Economic Cooperation and Development).

Diagnostic test: Any procedure performed on a sample collected from a subject, wherein the procedure can be used to evaluate or monitor a disease or a disorder in the subject. A diagnostic test can be performed in a laboratory, a medical office or in the home environment.

Flushable: A product's capacity to pass through typical commercially available house toilets and plumbing drainage systems without causing clogging or similar problems that can be directly associated with the physical characteristics of the product.

Larger and smaller portions: The major portion of the pad is a larger portion, and a minor portion is a smaller portion. Large and small can be defined, for example, in terms of cross-sectional area, volume, or transverse dimension. In some embodiments, the pad is inserted between the labia with the minor portion as the leading edge inserted, in which example the minor portion would also be considered an anterior edge and the major portion would be a posterior portion.

Medicinal Agent: A therapeutic agent for treatment of the interlabial space, perivaginal region, vagina, and/or for regional or systemic delivery. Specific, non-limiting examples of a medicinal agent are anesthetics, antibiotics, deodorants, or lubricants.

Supporting garment: A garment such as a belt or article of clothing, for example underwear, used to hold an absorbent pad in place on or in the body, for example in the vaginal triangle.

Vaginal orifice: The opening of the vagina at the perineum.

Figure 1:
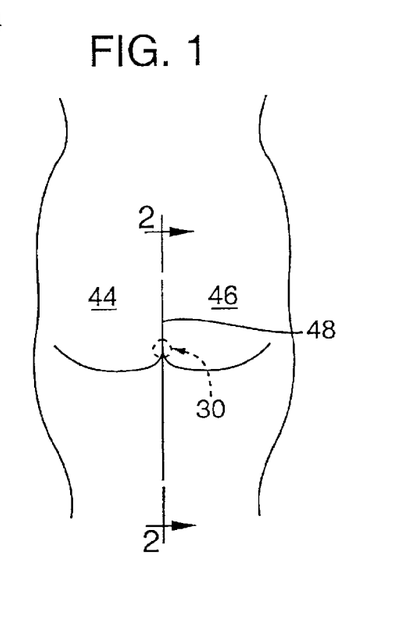
FIG. 1 is a schematic view of the perineum and thighs, which illustrates the external female genitalia.
Figure 2:
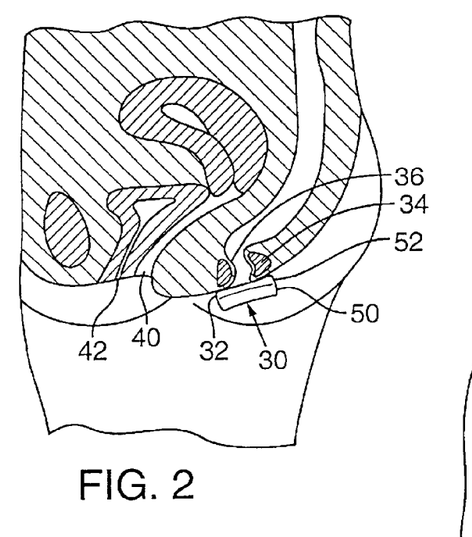
FIG. 2 is a cross-sectional sagittal view taken along line 2—2 of FIG. 1, but showing a pad positioned between the labia.
Figure 3:
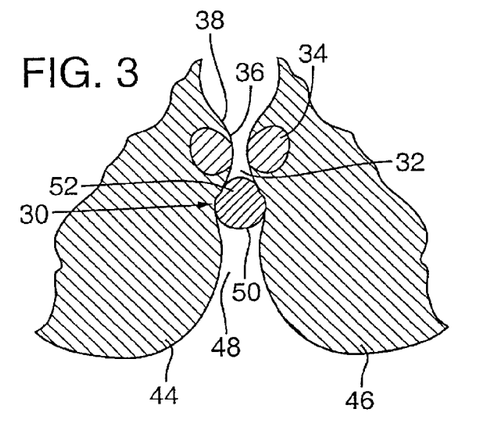
FIG. 3 is a schematic view of one embodiment of the interlabial drug delivery device.
Figure 3A:
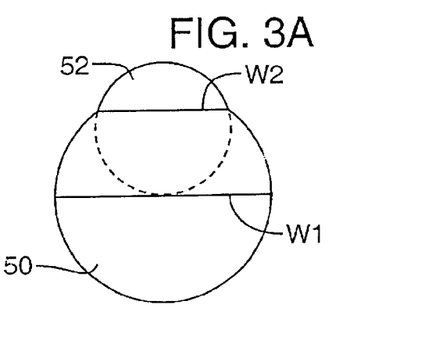

Embodiment of FIGS. 1–3

A first embodiment of the invention is shown in FIGS. 1–3. FIG. 1 illustrates the urogenital anatomy of a female. Interlabial space 32 is approximately bounded by the labia majora 34. Anatomical structures found within the interlabial space include the labia minora 36, vaginal orifice 38, urethral orifice 40, and clitoris 42. The perineum is a term that often refers to the pelvic outlet that gives passage to the urogenital ducts and anus, but it is sometimes used in a more restricted sense to refer to the area 44 which lies between interlabial space 32 and the anus 46.

FIG. 2 is a sagittal section of female urogenital anatomy, and illustrates that in this embodiment of the invention, interlabial pad 30 is positioned in interlabial space 32 approximately adjacent labia majora 34, vaginal orifice 38, and urethral orifice 40.

In the embodiment disclosed in FIGS. 2–3, interlabial pad 30 is an elongated absorbent member, for example made of cotton, and has a bipartite profile with a major portion 50 and a minor portion 52. In the illustrated example, the major and minor portions each have a cross section that is a portion of a circle, where the portion of the circle of the major portion 50 has a greater diameter than the portion of the circle of the minor portion 52. The curvature of the minor portion is greater than the curvature of the major portion. The overall shape of pad 30 therefore includes a rounded major portion and a rounded minor portion, in which the transverse diameter or width W1 (FIG. 3) of the major portion is greater than the transverse diameter or width W2 of the minor portion, so that the width of pad 30 tapers in the direction of minor portion 52.

The width of major portion 50 is sufficient to fit comfortably and be retained without adhesives within the interlabial space. Minor portion 52 has a reduced width (and increased taper) to minimize pressure and discomfort in the area of vaginal and urethral orifices 32. The minimum width of minor portion 52 is, in some embodiments, substantially the same or slightly less than the maximum diameter of vaginal orifice 38. The outer profile of both the major and minor portions may be arcuate to help conform to surrounding body tissues. The cross-sectional area of minor portion 52 in some embodiments is less than 50% of the cross-sectional area of pad 30, and has a cross-sectional area that is, for example, 10 to 49% of the total cross-sectional area of pad 30.

The reduced width of minor portion 52 makes interlabial pad 30 easier to insert and use. Labia majora 34 and labia minora 36 are spread apart either by moving them apart, or by introducing the reduced width minor portion 52 as a leading edge of the pad between them, and advancing the pad toward vaginal orifice 38. As pad 30 is inserted into interlabial space 32, the leading minor portion 52 gradually moves labia majora and labia minora apart, to facilitate acceptance of major portion 50. Once minor portion 52 is in place against vaginal orifice and urethral orifice 32, major portion 50 provides an enlarged retention member that frictionally engages surrounding portions of labia majora 34 to retain medicinal interlabial pad 30 in position. In this position, interlabial pad 30 is able to deliver an effective amount of an agent to the interlabial space. The agent may provide its effect within the interlabial space, regionally, and/or systemically.

The pad is easily inserted between the labia majora and is easily retained in the interlabial space without the need for auxiliary retaining means. Thus, a light pressure on the major portion 50 will cause the smaller minor portion 52 to open the labia majora slightly and allow pad 30 to take its proper position in the interlabial space. The radii of the respective portions is such that the interlabial space 36 is substantially or completely occupied by the pad. The elongated pad extends along the interlabial space, such that the length of the pad helps frictionally engage the pad and enable it to resist dislodgement.

In particular embodiments, the pad is formed of a soft absorptive material such as cellulose, cotton, or another suitable natural or synthetic fiber or sheeting. In one embodiment the pad is flushable, and can be made of biodegradable material. The pad may be made as described in U.S. Pat. No. 5,575,047, herein incorporated by reference. This nonabsorptive material may enhance delivery of the medicinal agent from the pad to the interlabial mucosa, while minimizing absorption of vaginal fluids.

EXAMPLES OF ALTERNATIVE EMBODIMENTS OF PADS

Some other examples of alternative embodiments of the pad with a tapering portion are shown in FIGS. 4–28. Many of these embodiments are shown in cross-section as relatively flat, although they can be elongated (as indicated by the fragmentary depiction in each Figure).

In the embodiment shown in FIG. 4, a one piece absorptive pad 58 has a "tear-drop" or ovoid cross sectional shape which tapers progressively to a leading anterior edge portion 60 of limited transverse dimension from a posterior portion 62 of relatively large transverse dimension.

The pad 58 may be elongated transverse to the illustrated cross-section, or it may not be elongated (such that the length of the pad transverse to the cross section is less than the anterior-posterior dimension A-P of the cross-section). In elongated embodiments, the pad may be of uniform cross section along the length thereof, or may be tapered from one end to the other end thereof, and in particular embodiments is tapered in its anterior-posterior dimension AP. The user may readily and quickly insert the pad 58 into the interlabial space by introducing leading anterior portion 60 into the interlabial space. The pad is firmly self retained in the space and exhibits substantial absorptive capacity for discharges, and resists accidental dislodgement from the interlabial space.

Other embodiments of the pad are shown which have posterior major portions of a polygonal (for example quadrilateral) shape, such as rectangular or square. Thus, as shown in FIG. 5, pad 62 includes a posterior portion 64 having flat bottom and side surfaces; and the anterior minor portion 66 has surfaces 68 which incline toward one another toward a leading edge 70. Anterior portion 66 therefore forms a wedge that parts the labia as it is introduced between them.

FIG. 6 shows a pad 72 that includes a posterior portion 74 of substantially square cross section; and a fingerlike anterior portion 76 of limited transverse dimension, which is much narrower than the corresponding transverse dimension of posterior portion 74. The juncture 78 of portions 74, 76 forms an essentially flat shoulder that extends transverse to the anterior-posterior dimension AP. In the disclosed embodiment, the anterior-posterior dimension of anterior portion 76 is substantially the same as the anterior-posterior dimension of posterior portion 74. The slender projecting finger of this pad can be configured to project through the vaginal orifice and into the vagina when the interlabial pad is in place. As discussed in detail below, the projecting finger can carry a pharmaceutical agent designed for vaginal delivery.

FIG. 7 shows a pad 80 that is similar to that of FIG. 8, except that the sides of anterior portion 84 diverge away from top edge 86, to present a more tapered profile. FIG. 8 shows a pad 88 having a posterior portion 90 and an anterior portion 92, wherein both portions are substantially quadrilateral in shape, except for a sloping flat shoulder 94 at the juncture of portions 90, 92. FIG. 9 shows a pad 95 that includes a posterior portion 96 of quadrilateral shape and an anterior portion 98 having upwardly converging side surfaces 100 and a flat leading edge 102.

While the pads shown in FIGS. 5–9 have posterior portions with flat bottom surfaces, the bottom surfaces may have other configurations. Thus, as shown in FIG. 10, the posterior portion P has an arcuate bottom surface A, while in FIG. 11, the posterior portion P' has converging surfaces C and an arcuate bottom edge B.

Further, alternative embodiments are shown in FIGS. 12 and 13. Thus, in FIG. 12, the non-bipartite pad 104 is of generally triangular cross section, with a posterior portion 106 of large cross section and an anterior portion 108 of small cross section. The pad 104 has flat, converging surfaces 110, a slightly curved bottom surface 112, rounded bottom edges 114 and a rounded leading edge 116. The pad 118 shown in FIG. 10 is similar to pad 106, except that the anterior portion 120 is transversely constricted and provides a linear juncture J between posterior portion 122 and anterior portion 120. This is an example of a bipartite pad that has major and minor portions.

FIG. 14 shows pad 124 which includes a posterior portion 126 of substantially hexagonal cross section and a transversely constricted anterior portion 128 with a rounded leading edge 130. The surfaces of posterior portion 126 are flat and edges thereof may be rounded.

FIG. 15 shows pad 132 which includes a posterior major portion 134 defined by opposed convergent flat surfaces 136 and a slightly rounded bottom surface 138; while anterior minor portion 140 is of a triangular cross section.

The pads may be suitably tapered in a longitudinal direction transverse to the AP direction. Thus pad 142, as shown in FIG. 16, has its anterior portion 144 and posterior portion 146 tapered in respect of both the longitudinal and transverse axes thereof; whereas in pad 148, as shown in FIG. 17, anterior portion 150 and posterior portion 152 are tapered longitudinally only.

Figure 18:
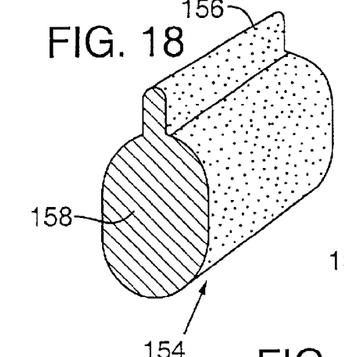
FIG. 18 is a perspective view of an elongated interlabial absorbent pad that has a fixed diameter along the length of the pad.

FIG. 18 shows yet another embodiment of the pad 154, in which the anterior portion 156 and posterior portion 158 are substantially ovoid in cross-section, with the transverse width of anterior portion 156 much less than the transverse width of posterior portion 158.

Figure 19:
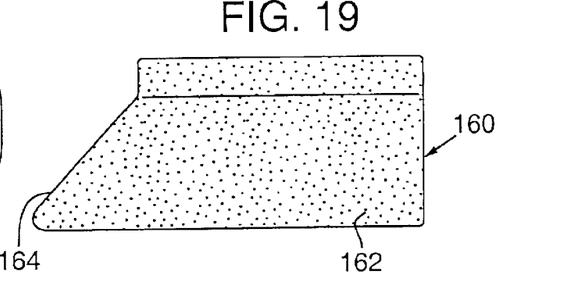
FIGS. 19–21 are side views of interlabial absorbent pads similar to the pad shown in FIG. 18, but with one or two sloping end edges.
Figure 20:
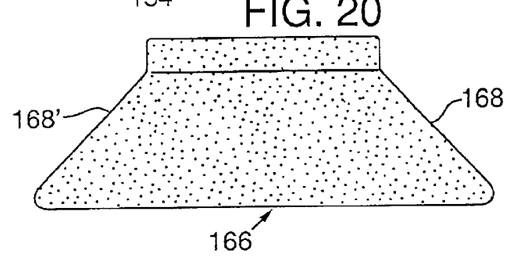
Figures 21, 23, 24, 25, 26, 27, 28:
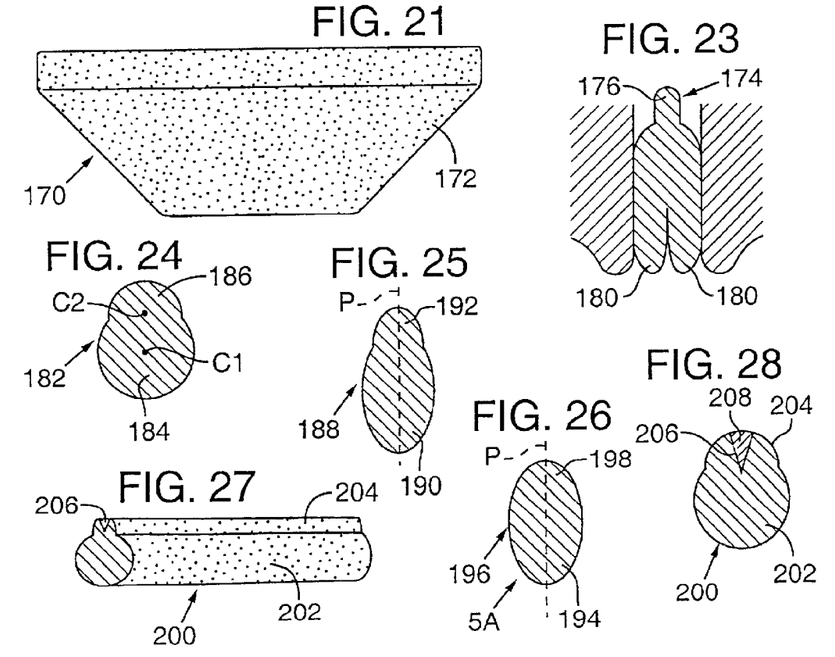
FIG. 23 is a cross sectional view of the interlabial absorbent pad of FIG. 22 disposed between the labia in the interlabial space.
FIG. 24 is a cross sectional view of a unitary, one-piece yet bipartite interlabial absorbent pad in which each portion of the pad has a cross section of a portion of a circle, each circle having different radii of curvature.
FIG. 25 is a cross sectional view of a bipartite pad in which each portion of the pad has a cross section of a partial ellipse. The pads may be either symmetric or asymmetric. In the symmetric embodiment, the major and minor portions may have the shape of partial spheres or ellipsoids.
FIG. 26 is a cross sectional view of an additional embodiment of a one-piece interlabial pad with an elliptical cross section, and no minor and major portions.
FIG. 27 is an end perspective view of an elongated pad with a minor and a major portion that extends along its length, and a groove in the minor portion from which drugs or other agents can be released by compression of the pad in use.
FIG. 28 is an end view of the pad of FIG. 27.

The pads may be further modified, as shown in FIGS. 19–21. Thus, as shown in FIG. 19, the pad 160 has its posterior portion 162 sloped at one end as at 164, to make the pad conform to the anatomy of the user. Alternatively, as shown in FIG. 20, the pad 166 may be sloped at both opposite ends 168, 168'. Alternatively, as shown in FIG. 21, pad 170 has its posterior portion 172 sloped at opposite ends in a convergent configuration. If desired, in the foregoing embodiments, the anterior portions of the pads may also be sloped to converge toward one another.

Figure 22:
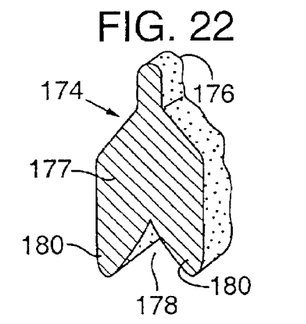
FIG. 22 is a cross sectional view of an interlabial absorbent pad wherein the posterior portion of the pad is formed with a longitudinal groove.

FIG. 22 shows an embodiment of a pad 174 that has an anterior portion 176 and posterior portion 177. The posterior portion 177 is formed with a longitudinal groove 178 of normally triangular section, forming wings 180. When the pad 174 is inserted into the interlabial space, as shown in FIG. 23, the wings 180 are resiliently urged toward each other and bear against the labia majora, thereby increasing the retention of the pad within the interlabial space.

The various forms of pads set forth above may also include the groove in the anterior portions thereof. The pads set forth above which have opposed flat surfaces (e.g. FIGS. 6–9), are particularly adapted to conform to the medial surfaces of labia majora, thereby optimizing pad retention and drug delivery. Such embodiments that have slender projecting anterior portions can also be configured such that the anterior projection inserts into the vaginal opening, to further enhance retention of the pad, or delivery of an agent to the vagina.

Although some of the pads have been shown to taper longitudinally from one end to the other end, they may also taper from a central portion to the opposite ends thereof. Thus, while the pad may be of uniform cross section throughout its length, it may also have a tapered form. No string or other removal aid is required, and the pad can be removed manually, such as with a gentle tap.

Another embodiment of the medicinal interlabial pad 182 is shown in FIG. 24, in which the pad 182 has a posterior portion 184 and anterior portion 186, each having a cross section that defines a portion of a circle. Each of the posterior and anterior portions is a portion of a sphere that is symmetric in all directions with respect to a center point, and has a constant radius. For example, posterior portion 184 is symmetric with respect to center C1, while anterior portion 186 is symmetric with respect to center C2.

FIG. 25 shows yet another embodiment of a pad 188 having merged portions 190, 192 which are of part elliptical cross section; the portion 190 having major and minor axes somewhat larger then those of portion 192, which also lends itself to easy insertion and removal. Portion 190 is symmetric in all directions with respect to perpendicular planes of symmetry, one of which is shown as P in FIG. 25. In this embodiment, the pad is not elongated in any direction, although in other embodiments longitudinal elongation is possible.

The pad 194, shown in FIG. 26, is of an elliptical cross section. This embodiment lacks a major portion and a minor portion, and instead has a cross-section that is completely symmetric with respect to an anterior-posterior plane AP. In use, pad 194 is inserted along the AP axis into the interlabial space (either narrowed end of the pad can be the leading edge of insertion).

The pad 190 shown in FIG. 27 is an elongated version of the pad in FIG. 24 which has a more spherical configuration. Pad 190 in FIG. 27 is initially of a round cross section, but is formed into a larger and smaller portion by using a mechanical binding agent, such as thread or heat welding, similar to that described in Gerstenburger (U.S. Pat. No. 5,575,047). Alternatively, it can be sewn along the junction between the two portions with biodegradable thread, so that the pad is completely biodegradable, and can be flushed down a toilet. Biodegradable pads can be made by any method, such as those disclosed in U.S. Pat. No. 5,575,047, which is incorporated herein by reference.

In certain examples, the absorbent pads are additionally (or alternatively) impregnated with selected scents, to mask the odor of the medication or any discharges, thereby providing a soothing and pleasant odor. In one embodiment, the pad is impregnated with medication in the anterior (or minor) portion only (that fits closest to the vaginal opening), or in the posterior portion only. In other embodiments, both the anterior (or minor) and posterior (or major) portions are impregnated with the medication. Alternatively, the anterior portion may be impregnated with medication, and the posterior portion is impregnated with an odor absorbing or masking agent, or vice versa.

In one embodiment, the pad includes a groove in the anterior or posterior portion, and the scent, medication, or another agent is added within the groove or impregnated in the pad adjacent to the groove. However, in other embodiments the medication is introduced into the pad by applying it as a liquid or powder to the pad. Depending on the dosage to be administered, the condition to be treated, the medication to be dispensed, and other factors, the drug or other active agent can be introduced on to the surface of the pad, impregnated throughout it, or introduced into superficial regions of the pad, or parts of it.

FIG. 27 shows a cross-section of an embodiment of an elongated absorbent pad 200 that has been modified to carry and dispense pharmaceutically active agents alone or in admixture with deodorants, lubricants, and the like. The principles of the elongated embodiment could, however, be adapted to the non-elongated embodiments of the type shown in FIG. 24. In the embodiment shown in FIG. 27, pad 200 includes posterior portion 202 and anterior portion 204, which is formed with a groove 206 extending longitudinally along the top of anterior pad portion 204. The groove is prefilled with a material 208, for example, with an ointment, lubricant or other carrier for admixed medications, deodorants and the like. Placing the interlabial pad in the interlabial space, with anterior portion 204 adjacent to the vaginal orifice and urethral orifice, causes the normal transverse constriction of the pad 200 (and particularly compression of anterior portion 204) to dispense materials which have a suitable viscosity, to the interlabial space, and to the vagina which opens into the interlabial space.

It has been found that the curvilinear surface portions and the non-uniform cross sections of the several pads shown herein, is highly effective in positioning the pad in the interlabial space and retaining it in place. Further, there is no tendency to uncomfortably force the labia majora apart or to exert undue pressure against their medial wall portions.

In an additional embodiment, the pads are used to absorb discharge from the structures within the interlabial space, such as the urethra, vagina, and vulvar epithelium. A diagnostic test is then performed on the absorbed discharge. In one embodiment, the discharge is a bodily fluid, such as blood or a secretion, such as a secretion derived from the reproductive system. In yet another embodiment, the discharge includes cells, such as cells of the vulvar, vaginal or cervical epithelium, and the cells are analyzed using a diagnostic test. The diagnostic test can be performed directly on the discharge absorbed by the medicinal interlabial pad, or the discharge or a component of the discharge can be extracted from the interlabial pad prior to performing the diagnostic test (see U.S. Pat. No. 5,094,956).

The diagnostic test can detect, for example, the presence or absence of a cell type (e.g. see U.S. Pat. No. 5,124,252; U.S. Pat. No. 5,965,375), a protein (e.g. see U.S. Pat. No. 5,190,881; U.S. Pat. No. 5,661,010), or a nucleic acid (e.g. see U.S. Pat. No. 5,538,851; U.S. Pat. No. 5,459,034) in the vaginal discharge. The diagnostic test can also be used to detect blood (see U.S. Pat. No. 4,920,045; U.S. Pat. No. 5,563,071), or the presence of a virus, such as human papillomavirus (HPV), or a microorganism, such as a pathogen (see U.S. Pat. No. 5,705,332; U.S. Pat. No. 5,627,275). The diagnostic test can be a qualitative, semi-quantitative, or quantitative test. In one specific, non-limiting example, the diagnostic test is used to detect a biological parameter associated with cervical cancer.

In a specific, non-limiting example, vaginal and vulvar discharge is collected on the pad and a diagnostic test is then performed on the discharge to detect human papillomavirus (HPV) infection. For example, the diagnostic test can detect the presence of HPV nucleic acid (see U.S. Pat. No. 5,580,907; U.S. Pat. No. 5,876,922; U.S. Pat. No. 5,783,412; U.S. Pat. No. 5,447,839; U.S. Pat. No. 5,283,171). Alternatively, the diagnostic test can detect the presence of a protein associated with HPV infection (see U.S. Pat. No. 5,045,447).

In one embodiment, a kit is provided for administering the medication from the drug delivery device. The kit includes an interlabial pad, and a package such as a plastic vial or a plastic or foil container, for packaging the interlabial pad. The kit can also include directions for the use of the pad. The pad can contain a unit dose of the medication, for example an anti-infective, such as gynelotrimin. Another example is the delivery of estradiol to treat vaginal atrophy or for hormone replacement therapy (HRT). In HRT, and ILP system releasing 100 mg/day of estradiol as its 3-acetate ester maintaines a circulating plasma concentration of 300 pmol/L of the drug, which is within the clinically desirable range for HRT.

Examples of other therapeutic agents that could be delivered using this system are the delivery of 20 micrograms/day ethinyl estradiol to hypoestrogenic subjects for peak bone mass acquisition during adolescence; 200 micrograms/day of 17 β-estradiol to relieve severe post-menopausal symptoms; 400 micrograms/day of the GnRH agonist nafarelin for 4 weeks in the initial treatment of endometriosis, followed by half-dose therapy (200 micrograms/day) for 20 weeks; local delivery of levofloxacin for ther treatment of chlamydia trachomatis; or delivery of 1% flutrimazole for the treatment of fungal infections.

Figure 29:
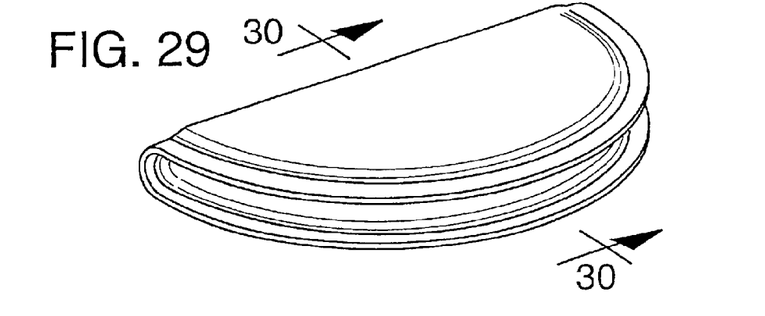
FIG. 29 is a perspective view of an elongated folded pad.
Figure 30:
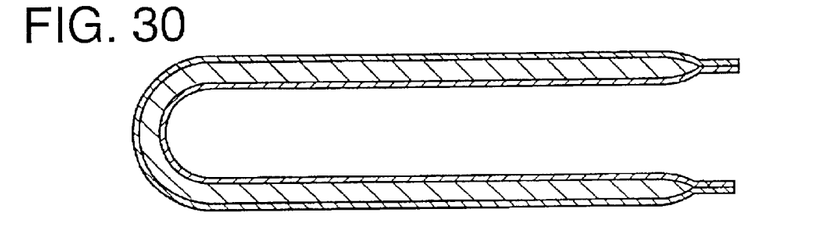
FIG. 30 is an end view of the pad of claim 29.
Figure 31:
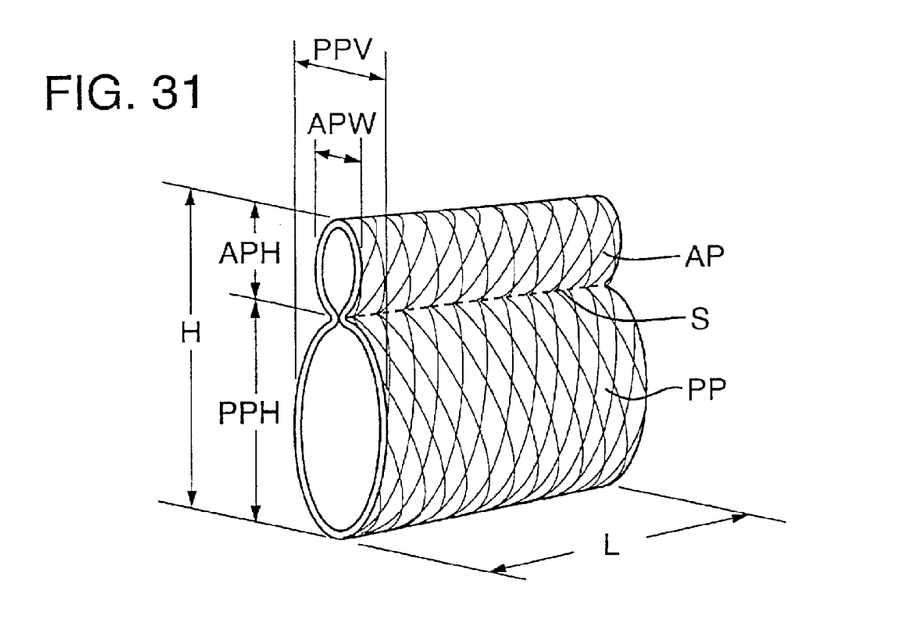
FIG. 31 is a perspective view of an elongated pad.

FIG. 29 shows a particular embodiment wherein an interlabial pad is formed of a polypropylene or polyester nonwoven fabric with a rayon sliver core. The interlabial pad has an overall length L of about 15 to about 75 mm, and an overall height H of about 19 to about 22 mm. Of the overall height of the interlabial pad, the anterior portion AP of the interlabial pad has a height APH of about 4 to about 7 mm. The posterior portion PP of the interlabial pad has a height PPH of about 12 to about 18 mm. In addition, posterior portion PP of the pad has a width PPW of about 8 to about 10 mm. Anterior portion AP has a width APW less than width PPW of posterior portion PP of the pad. In one specific, non-limiting example, width PPW of posterior portion PP of the interlabial pad is from about 4 to about 7 mm. Posterior portion PP of the pad is demarcated from anterior portion AP of the pad by stitching S. In one specific, non-limiting example the stitching is standard 401 chain stitch of about 8–10 SPI.

Example 1

Method of Making the Pad

In one embodiment the application devices, such as pads, are molded or otherwise formed from the cellulose base material, to the desired cross sectional and longitudinal configurations by apparatus and procedures known in the art, or formed as described in Gerstenburger. The active agent (such as the drug or diagnostic reagent) can, for example, be applied in a liquid form by a liquid applicator, between the dancer and puller.

Figure 33:
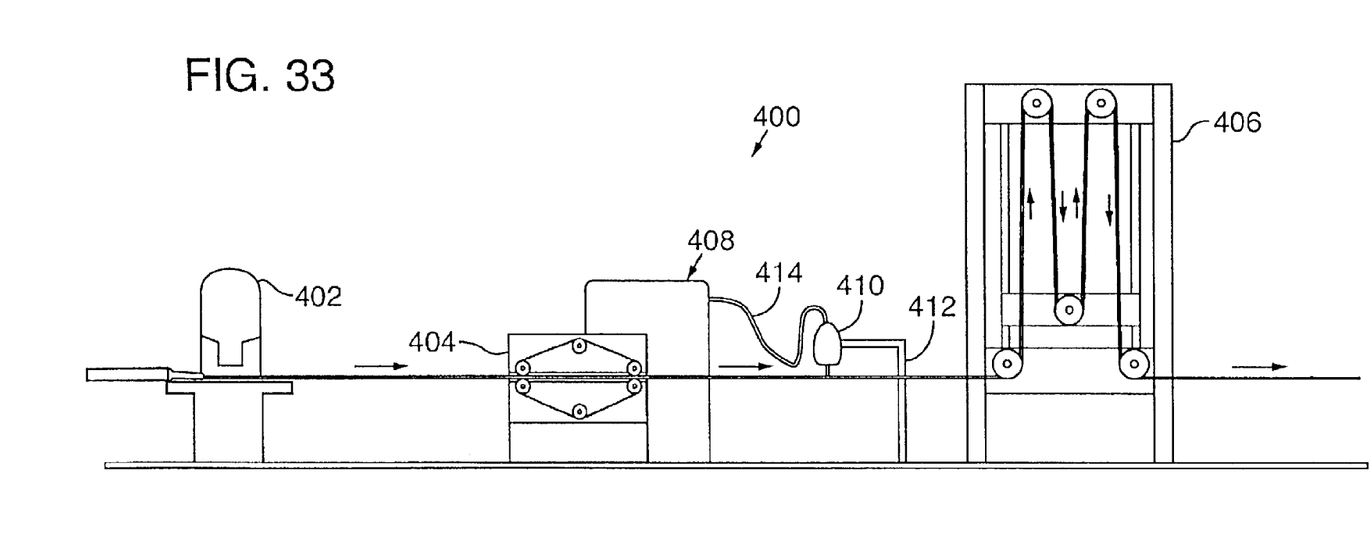
FIG. 33 is a schematic diagram of a system for making the application devices.

A specific example of a liquid application system 400 is shown in FIG. 33, in which the rope to make a pad passes through a sewing station 402, a puller 404, and a dancer 406. Interposed between puller 404 and dancer 406 is a liquid applicator 408, which includes an applicator head 410, mounted on a stand 412, and connected to a source of liquid through a flexible conduit 414.

Figure 34:
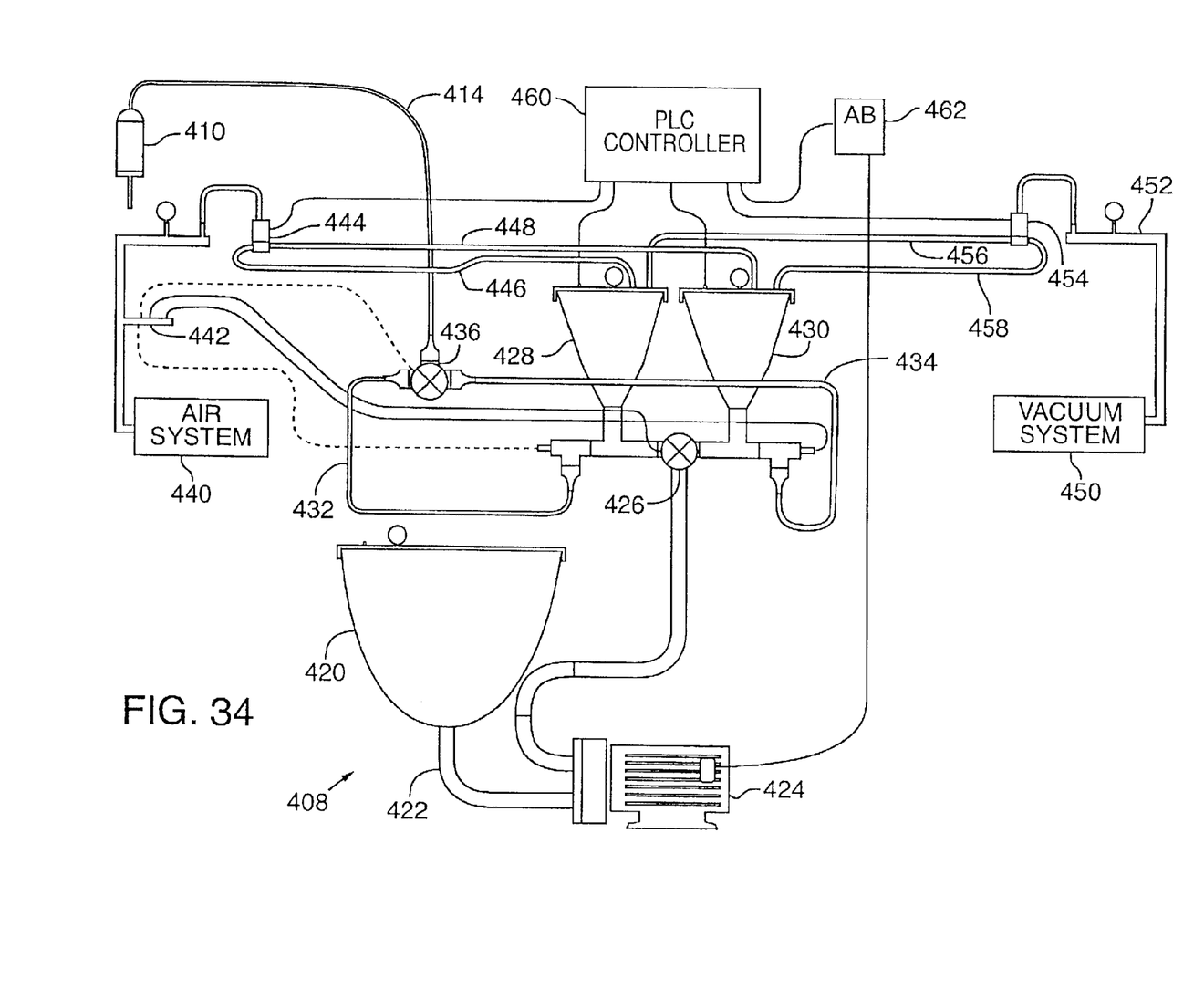
FIG. 34 is a schematic diagram of a liquid application system for applying liquid agents to the application devices.

A more detailed example of liquid application system 400 is illustrated in FIG. 34, which includes a bulk tank 420 to hold the liquid to be applied, a conduit 422 connecting tank 420 to a pump motor 424 and a 3 way valve 426, which controls access to a pair of dispensing tanks 428, 430. Liquid application lines 432, 434 lead from opposite ends of valve 426 to a dispensing three-way valve 436, which in turn communicates with flexible conduit 414 that leads to applicator head 410.

A source of pressurized air 440 is connected through an air manifold 442 to a pressure valve 444, which controls flow of pressurized air through pressure lines 446, 448 that communicate respectively with dispensing tanks 428, 430. A vacuum generator 450 is also connected through a vacuum manifold 452 to a vacuum valve 454, which controls drawing a vacuum through vacuum lines 456, 458 that communicate respectively with dispensing tanks 428, 430.

A computer operated controller 460 controls applicator system 408, and integrates its operation into the operation of the pad manufacturing process. In particular, controller 460 communicates with a motor controller 462, which in turn communicates with pump motor 424. The controller also communicates with and controls the other components of system 408, such as dispensing tanks 428, 430, pressure valve 444, and vacuum valve 454.

In operation, controller 460 actuates pump 424 to draw liquid from bulk tank 420 and introduce it into dispensing tanks 428 or 430, depending on the position of valve 426. Vacuum generator 450 can also be actuated to remove air from the tank prior to introduction of liquid into dispensing tanks 428, 430, to facilitate filling of the tanks. Sensors within dispensing tanks 428, 430 determine when the tanks are full, and send this information to controller 460 to turn off motor 424. Controller 460 can actuate pressurized air source 440 to introduce pressurized air into dispensing tanks 428, 430 to assist in the flow of liquid from the tanks through valve 436 and into flexible conduit 414. The pressurized liquid is then sprayed out of dispensing head 410 on to the pad. Since controller 460 also monitors the manufacturing line, the rate of application of the liquid can be increased or decreased corresponding to an increase or decrease in the speed of the production line.

Example 2

Method of Using the Pad

In use, some embodiments of the application device, such as the pad, would be inserted into the interlabial space and retained for a sufficient period of time to deliver the active agent, or allow sufficient time for reaction with a diagnostic reagent. If the active agent is a diagnostic agent (such as a monoclonal antibody), then the pad could be retained for a period of minutes to allow the reaction to occur. If the agent is a drug intended for topical application (such as the anti-fungal agent miconazole), then the pad is retained in place for a sufficient period of time, for example 30 minutes to 4 hours, to allow the miconazole to be transmitted to the adjacent labial skin and vagina. Alternatively, if the drug is intended for transdermal delivery (for example of estrogen) then a longer period of transfer may be desired, in which the pad is retained for at least one or two hours. If the pad is removed before the desired period of time has elapsed (for example because the subject needs to urinate), then it can be temporarily removed and replaced. Alternatively, a new pad can be inserted.

In other embodiments, a topical preparation is applied to the labia, followed by insertion and retention of an interlabial pad to retain the topical preparation (such as a cream or ointment) in contact with the skin, and inhibit transfer of the medication to clothing or adjacent skin. Alternatively, a medicated vaginal suppository is inserted intravaginally, and the device is placed intra-labially to inhibit loss of medication, or soiling of garments. In yet other embodiments, the device includes an intravaginal portion (such as a suppository, an intravaginal portion of the pad, or an intravaginal probe) which delivers a therapeutic or diagnostic agent intravaginally, and an extravaginal portion (such as an ILP) which helps retain the device in place, and prevents loss of the agent from the vaginal opening.

In view of the many possible embodiments to which the principles of the invention may be applied, it should be recognized that the illustrated embodiments are only particular examples of the invention and should not be taken as a limitation on the scope of the invention. Rather, the scope of the invention is defined by the following claims. We therefore claim as our invention all that comes within the scope and spirit of these claims.

I claim:

1. An interlabial delivery device comprising a delivery pad, wherein the pad is configured to be retained between labia of a subject, and the pad carries a therapeutically or diagnostically effective amount of a diagnostic or therapeutic agent;

wherein the pad has a minor portion superimposed on a major portion, the minor portion having a cross-sectional area smaller than a cross-sectional area of the major portion and wherein the minor portion is tapered to facilitate insertion between the labia and retention in the interlabial space, wherein the pad includes a cavity in an external surface of the pad, wherein substantially all the diagnostic or therapeutic agent is contained within the cavity.

2. The device of claim 1, wherein the agent is a transdermal agent.

3. The device of claim 1, wherein the pad is a highly absorbent non-swellable material.

4. The device of claim 1, wherein the pad is elongated to extend along the interlabial space to frictionally engage the pad against the labia and enable the pad to resist dislodgement.

5. The device of claim 1, wherein the agent is a drug in a unit dosage form.

6. The device of claim 1, wherein the minor and major portions of the pad have an elliptical cross-section with a major axis, wherein the major axis of the minor portion is less than the major axis of the major portion, and the major axis is of a sufficient size to retain the device substantially completely external to a vaginal orifice.

7. The device of claim 1, wherein the delivery material includes an agent for absorbing odors.

8. The device of claim 1, wherein the agent is a diagnostic agent.

9. The device of claim 1, wherein the agent is a therapeutic agent.

10. The device of claim 1, wherein the delivery device comprises an intravaginal portion and an extravaginal portion, and the intravaginal portion carries the agent to be delivered.

11. The device of claim 1, wherein the agent is an antibiotic or anti-fungal agent.

12. The device of claim 1, wherein the agent is a hormone.

13. A method for administering a drug to a subject, comprising inserting a pad impregnated with the drug into the subject's interlabial space, positioning the pad against the subject's external vaginal orifice, wherein the pad is devoid of corners and flat surfaces, and the pad has a minor portion superimposed on a major portion, the minor portion having a cross-sectional area smaller than a cross-sectional area of the major portion, wherein both the minor and the major portion are curvilinear in cross-section, and wherein the minor portion facilitates insertion between the subject's labia and retention in the interlabial space; and retaining the pad in the interlabial space to dispense the drug interlabially, wherein the pad includes a recess that extends along an exterior surface of the pad, and in which the drug is placed, wherein compression of the pad compresses the recess to dispense the drug.

14. The method of claim 13, wherein the pad is elongated and has a uniform cross-section along its entire length, or is tapered along its length.

15. The method of claim 13, wherein the pad is elongated, and when placed in the interlabial space to dispense the drug, extends completely external to the vaginal orifice.

16. The method of claim 13, wherein the pad carries a therapeutically effective amount of a medicinal agent, and positioning the pad comprises administering the medicinal agent to the subject.

17. The method of claim 13, wherein the medicinal agent is an antifungal agent or a hormone.

18. The method of claim 13, wherein the minor and major portions of the pad have a length greater than their width, and the shape of the pad substantially conforms to the interlabial space in which the pad is retained.

19. The method of claim 18, wherein the pad is held between the labia without adhesive or attachment to a supporting garment.

20. The method of claim 13, wherein the major portion of the pad has longitudinally extending, opposed, substantially parallel face portions.

21. The method of claim 20, wherein the minor portion of the pad has longitudinally extending, opposed substantially parallel face portions.

22. The method of claim 21, wherein the opposed flat face portions of the pad are substantially parallel.

23. The method of claim 22, wherein the opposed flat face portions of the pad are substantially convergent.

24. The method of claim 13, wherein the minor portion of the pad has longitudinally extending, opposed substantially parallel face portions.

25. The method of claim 24, wherein the opposed flat face portions of the pad are substantially parallel.

26. The method of claim 24, wherein the opposed flat face portions of the pad are substantially convergent.

27. The method of claim 13, wherein the minor and major portions of the pad have a shoulder shaped junction.

28. The method of claim 13, wherein the pad carries a therapeutically effective amount of a medicinal agent, and positioning the pad comprises administering the medicinal agent to the subject to relieve the symptom.

29. The method of claim 28, wherein the medicinal agent is an anti-microbial or a hormone.

30. The method of claim 13, wherein the pad includes a cavity in which a medicinal agent is placed prior to positioning the pad.

31. The method of claim 30, wherein the cavity is compressed between the labia when the pad is positioned.

32. The method of claim 31, wherein the cavity communicates with an exterior surface of the pad.

33. The method of claim 32, wherein the cavity is a recess in an exterior surface of the minor portion of the pad.

34. The method of claim 33, wherein the pad is elongated, and the cavity extends longitudinally along the pad.

35. The method of claim 13, wherein the method further comprises applying medication intravaginally or perilabially prior to or simultaneously with positioning the pad.

* * * * *